(12) United States Patent
Lyu et al.

(10) Patent No.: US 8,637,064 B2
(45) Date of Patent: Jan. 28, 2014

(54) COMPRESSION MOLDING METHOD FOR MAKING BIOMATERIAL COMPOSITES

(75) Inventors: SuPing Lyu, Maple Grove, MN (US); Christopher M. Hobot, Tonka Bay, MN (US); Sean M. Haddock, Memphis, TN (US); Brian A. Loy, New Brighton, MN (US); Randall V. Sparer, Andover, MN (US); K. Matthew Kinnane, Bartlett, TN (US); Jeffrey M. Gross, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 813 days.

(21) Appl. No.: 11/523,841

(22) Filed: Sep. 20, 2006

(65) Prior Publication Data

US 2008/0069856 A1 Mar. 20, 2008

(51) Int. Cl.
*A61F 2/00* (2006.01)

(52) U.S. Cl.
USPC ........................................................ 424/423

(58) Field of Classification Search
USPC ........................................................ 424/423
See application file for complete search history.

(56) References Cited

U.S. PATENT DOCUMENTS

| | | | |
|---|---|---|---|
| 4,743,257 A | 5/1988 | Tormala et al. | |
| 5,433,751 A | 7/1995 | Christel et al. | |
| 5,522,895 A | 6/1996 | Mikos | |
| 5,529,736 A | 6/1996 | Shalaby et al. | |
| 5,866,155 A * | 2/1999 | Laurencin et al. | 424/425 |
| 6,022,509 A | 2/2000 | Matthews et al. | |
| 6,203,573 B1 | 3/2001 | Walter et al. | |
| 6,241,771 B1 | 6/2001 | Gresser et al. | |
| 6,548,002 B2 * | 4/2003 | Gresser et al. | 264/229 |
| 6,673,075 B2 | 1/2004 | Santilli | |
| 6,696,073 B2 | 2/2004 | Boyce et al. | |
| 6,908,582 B2 | 6/2005 | Shikinami et al. | |
| 2004/0099979 A1 * | 5/2004 | Chen et al. | 264/41 |
| 2005/0008620 A1 * | 1/2005 | Shimp et al. | 424/93.7 |
| 2005/0246021 A1 | 11/2005 | Ringeisen et al. | |
| 2005/0251267 A1 | 11/2005 | Winterbottom et al. | |

FOREIGN PATENT DOCUMENTS

| | | |
|---|---|---|
| EP | 0 988 839 B1 | 1/2005 |
| WO | WO03064509 A2 | 8/2003 |
| WO | WO2004053112 A | 6/2004 |

OTHER PUBLICATIONS

Tetrahydrofuran 2008. MSDS from JTBaker.*
Zhou et al. 1993. High temperature characteristics of synthetic hydroxyapatite. J. Materials in Science. 4:83-85.*
Jeon et al. Effect of solvent on the preparation of surfactant-free poly(DL-lactide-co-glycolide) nanoparticles and norfloxacin release characteristics. International Journal of Pharmaceutics 207 (2000) 99-108.*
International Search Report for European ApplicationNo. PCT/US2007/078606 mailed on Mar. 11, 2009.
Jing D., Wu L. and Ding J., "Solvent-Assisted Room-Temperature Compression Molding Approach to Fabricate Porous Scaffolds for Tissue Engineering", Macromol. Biosci., vol. 6, Sep. 15, 2006, pp. 747-757, XP002516225 the whole document.

* cited by examiner

*Primary Examiner* — Taeyoon Kim
(74) *Attorney, Agent, or Firm* — Sorell Lenna & Schmidt LLP

(57) ABSTRACT

A process for making an implantable material comprising a composite of a biocompatible polymer and a bioactive agent. The composite combines desirable mechanical properties of polymers and the bioactivity of tissue or one or more component of tissue. More particularly, but not exclusively, the invention relates to methods for the manufacture of implantable materials, devices and components via a powder molding process.

16 Claims, No Drawings

COMPRESSION MOLDING METHOD FOR MAKING BIOMATERIAL COMPOSITES

The present invention relates to the field of biomedical implants and, in particular, implantable materials comprising a composite of a biocompatible polymer and a bioactive agent. The composite combines desirable structural/mechanical properties of polymers and bioactivity of tissue, tissue components or other bioactive agents. More particularly, but not exclusively, the invention relates to methods for the manufacture of implantable materials, devices and components using a powder molding process.

BACKGROUND

The use of bone grafts and bone substitute materials in orthopedic medicine is well known. While bone wounds can regenerate, fractures and other orthopedic injuries take a substantial time to heal, during which the bone is unable to support physiologic loads. Metal pins, screws, plates, rods, and meshes are frequently required to replace the mechanical functions of injured bone during the time of bone healing and regeneration; however, metal is significantly stiffer than bone. Use of metal implants may result in decreased bone density around the implant site due to stress shielding. Additionally, metal is less than ideal as an implant material because it remains at the healing site after healing has occurred and the need for the metal implant has passed.

The structural requirements placed upon orthopedic devices are even more pronounced when considering implants that are required to provide structural support to a human spine. Spinal fusions require interbody fusion devices that will maintain significant structural rigidity for at least 6-12 months, and strength requirements depend on the location of the disc to be replaced. When a person is standing, the forces to which a disc is subjected are much greater than the weight of the portion of the body above it. It has been reported that the force on a lumbar disc in a sitting position is more than three times the weight of the trunk.

During the course of a bone's cellular healing processes, through coordinated activity of osteoblast and osteoclast cells, bone grafts and certain bone substitute materials placed at the site of an injury can be removed by natural processes over time and replaced by endogenous bone that is almost indistinguishable from the original. An intact bone section harvested from a human donor can be formed into a monolithic bone graft in some cases; however, the use of such bone grafts is limited by the available shape and size of grafts and the desire to optimize both mechanical strength and replacement rate relative to the timeframe of fracture or defect healing at the skeletal site. Variations in bone size and shape among patients (and donors) also make monolithic bone grafts a less optimal substitute material.

Some bone substitute materials and bone chips can be used to form grafts of desired shape, and are quickly degraded, but such materials cannot immediately provide mechanical support. Cancellous bone allografts have open spaces for easy cellular penetration and biodegradation, but they lack appropriate initial strength for many load bearing applications. Cortical bone grafts are stronger than cancellous grafts but are more slowly and incompletely replaced by endogenous tissue. While the extent of integration of cortical bone grafts is generally considered adequate, it has been reported that endogenous replacement of such a graft seldom exceeds more than 50%. For these reasons, significant attention has been given in recent years to the development of orthopedic implant materials formed from polymeric materials that have mechanical properties approximating those of bone, i.e., that are suitable for load bearing, and that undergo extensive transformation into native tissue at a desirable rate.

While a number of polymeric materials have been developed and used for making implant composites, significant obstacles have been encountered. Traditionally, the processing of such polymers has been achieved via melt processing at temperatures high enough that the polymer is melted and can flow (typically 150 to 300° C.) or through solvent-aided processing in which the polymer is dissolved in a solvent, then molded and dried. A problem that has been encountered with the melt processing approach is that, though it is desired to incorporate bioactive materials, such as, for example, tissue-derived materials, into the implant, functionality (bioactivity) of many such materials is often compromised at the high processing temperatures of such protocols, and thus cannot be present during high-temperature processing of the polymeric phase. A problem with solvent-based processes is that a relatively long period of time is required to remove the solvent from the mixture. In addition, some solvents that would otherwise be useful to dissolve the polymers can compromise the functionality of bioactive materials.

With the development of a wide range of spinal prosthetic devices, and the use of a wide range of polymeric materials and bioactive agents to manufacture the same, there is a growing need for better ways to manufacture such devices. The present invention addresses this need.

SUMMARY

The present invention involves the discovery of new methods for making polymer-based, porous biological composites. Inventive processes can be used advantageously to make biologically active composites that have suitable mechanical properties for supporting structural loads within the human body, without using high temperature processing steps that would denature the bioactive material included therein. In certain preferred embodiments, biological composites made in accordance with the invention have biological functionality and have suitable structural integrity to be used as load-bearing spinal implants. The biological functionality can involve, for example, promotion of host tissue integration, such as, for example, ingrowth of bone after surgical implantation of the material in a patient, or perhaps up-regulation or down-regulation of other bio-remodeling processes. Inventive manufacturing methods achieve the advantageous result without using high temperature steps and without requiring the dissolution of the polymer materials a solvent.

The invention provides in one aspect a method for making a biomaterial composite that includes (1) providing a bioactive material that is stable up to a first temperature; (2) providing a particulate biocompatible polymer; (3) mixing the particulate polymer and the particulate bioactive material together with a binder to form a mixture, wherein the binder is effective to soften surfaces of the particulate polymer at a second temperature less than the first temperature; and (4) compressing the mixture at a third temperature less than the first temperature and greater than the second temperature for a period of time sufficient to allow at least a majority of the polymer particles to adhere to one another. In one preferred manner of practicing the invention, at the end of the period of time during which the compression is applied, the mold is cooled to room temperature or below room temperature under the compressive force.

In one preferred manner of practicing the invention, the bioactive material is a particulate material having an average particle size of less than about 80 microns. The bioactive material can be, for example, particulate bone. The particulate polymer preferably has an average particle size of less than about 500 microns. The ratio of polymer to bioactive material in the mixture by weight is preferably from about 1:2 (by weight) to about 9:1 (by weight). The compressing can comprise, for example, compressing under a compressive stress of from about 10,000 to about 30,000 PSI. The compressing is performed in certain preferred embodiments at a temperature between about 70° C. and about 100° C. In one preferred embodiment, the polymer is a polylactide polymer. A particularly preferred polymer for use in accordance with the invention is poly (L-co D,L-lactide).

The binder can advantageously be present in an amount effective to contact at least a majority of the polymer particles. In one preferred embodiment, the binder comprises a solvent in which the polymer is soluble and that does not destroy the bioactivity of the bioactive material. In yet another preferred embodiment, the solvent has a boiling point at or below the temperature at which the mixture is compressed. An excellent solvent selected for use in certain preferred embodiments is tetrahydrofuran. In another embodiment, the binder comprises a solution including a quantity of polymer dissolved in the solvent.

In another aspect of the invention there is provided a method for making a biomaterial composite that includes: (1) providing a bioactive material that is stable up to a first temperature; (2) providing a particulate biocompatible polymer; (3) mixing the particulate polymer and the particulate bioactive material together with a binder to form a mixture; and (3) compressing the mixture at a second temperature less than the first temperature for a period of time sufficient to allow at least a majority of the polymer particles to adhere to one another. The binder is a composition that is effective to soften surfaces of the particulate polymer at the second temperature.

An object of the present application is to provide a unique process for making bioactive porous plastic implant materials.

Further embodiments, forms, features, aspects, benefits, objects, and advantages of the present application shall become apparent from the detailed description and figures provided herewith.

DETAILED DESCRIPTION OF SELECTED EMBODIMENTS

For the purpose of promoting an understanding of the principles of the invention, reference will now be made to the embodiments set forth herein and specific language will be used to describe the same. It will nevertheless be understood that no limitation of the scope of the invention is thereby intended. Any alterations or further modifications of the described embodiments, and any further applications of the principles of the invention as described herein are contemplated as would normally occur to one skilled in the art to which the invention relates.

The present invention provides novel methods for making polymer-based, porous biological composites that do not require the use of high molding temperatures or the dissolution of polymeric starting materials in solvents. The structural portion of the composite is made from a particulate polymer starting material that is molded into a continuous, porous, polymeric matrix defining a network of internal passages in fluid communication with the article's environment through pores on the surface of the article. In order to produce a composite having good mechanical properties, the polymer particles are adhered (i.e., welded or sintered) to one another such that the polymer chains from different particles entangle with one another. In a composite implant material made in accordance with the invention, the porous plastic matrix contains a bioactive material (also referred to herein as "bioactive agent"). The material retains its bioactivity as it resides within the matrix, and produces a desired result after the material is implanted in a living body. The term "bioactive material" is used herein to refer to a compound or other composition of matter that has an effect on living tissues such as, for example, a composition that promotes an immune response, promotes cell proliferation, or has some other effect. In certain preferred embodiments, the bioactive material is effective to promote host tissue integration, such as, for example, ingrowth of bone, after surgical implantation of the composite material in a patient. Inventive low-temperature molding methods can be used to make composites having excellent structural integrity suitable for use, for example, as load-bearing portions of spinal implants, without having a detrimental impact on temperature sensitive bioactive agents included therein. Inventive methods achieve the advantageous result without using high temperature molding protocols or molding protocols that require dissolving the polymer in a solvent.

The invention is not intended to be limited to the manufacture of articles having a specific shape, or "macrostructure." Rather, a wide variety of shapes are envisioned. Indeed, composite materials made in accordance with the invention can be formed into a wide variety of shapes by original mold design, by post-molding processing or by a combination thereof, as discussed further herein. With respect to the internal structure, or "microstructure," of an inventive composite, raw materials and processing parameters can be selected in accordance with the invention to control the dimensions of the microstructure. The microstructure of a composite material made in accordance with the invention comprises a porous plastic matrix defining an internal network of passages, and defining "pores" in its exposed surfaces, which pores provide fluid communication between the internal passages and the material's environment. As used herein, the term "exposed surface" is intended to refer to a surface of the material with which body tissues come into contact after implantation. Stated alternatively, an exposed surface is defined with respect to the material's macrostructure as a surface which defines the shape of the material and which generally defines the boundary between the material and its environment.

An "internal passage" or an "internal network of passages" refers to the microstructure of a composite material made in accordance with the invention, and refers to spaces defined internally, i.e., within the porous plastic matrix. As is readily understood by a person skilled in the relevant art, characteristics of internal passages may be varied by varying, for example, the size of polymeric particles used to make inventive composites and/or the temperature and/or the pressure used in a molding process for making the material. An implant is made in accordance with the invention such that a porous plastic matrix, having a network of internal, interconnected passages therein, holds a bioactive material until the implant is surgically implanted in a body, at which time the bioactive material is effective to have a desired affect on the surrounding tissue.

To make an inventive article in accordance with one embodiment of the invention, a mixture of a granular, or particulate, thermoplastic polymer, a bioactive agent and a binder material is provided and the mixture is then molded at a predetermined temperature and pressure to make an inventive article. In a preferred embodiment, the binder is present in an amount effective to contact a majority of the polymer particles present in the mixture.

A wide variety of molding techniques can be used in accordance with inventive methods, such techniques being known in the art. While it is not intended that the present invention be limited by any theory by which it achieves its advantageous result, it is believed that, under molding conditions applied in accordance with the invention, the outer surfaces of the polymer granules become softened or tacky. When this occurs, pressure exerted upon the mixture causes the polymer granules to contact one another and adhere together. After the molding process is complete, the points of contact become relatively strong points of adhesion, thus providing a strong composite that is suitable for use as an orthopedic implant device. The temperature at which the compression is applied is a temperature less than that which would damage or denature the bioactive agent but high enough to achieve a desired level of polymer particle adhesion.

It is understood that a wide variety of material specifications (such as polymer type, polymer size, granule size distribution and ratio of polymer to bioactive agent) and also a wide variety of process parameters (such as temperature and pressure) may be used in accordance with the invention to provide articles having various advantageous characteristics. For example, inventive articles may be made in accordance with the invention that have differing rates of release of a bioactive agent into surrounding tissues after implantation or that initiate biochemical responses at different rates. These rates can be controlled in part by controlling the dimensions of the internal passages and pores, which in turn can be controlled by varying the material specifications and process parameters described herein. It is within the ability of a skilled artisan, armed with the description of the present invention, to select, without undue experimentation, advantageous combinations of materials and parameters in accordance with the invention to provide articles having differing rates of bioactive release.

It is important in inventive methods that the polymer particles, or granules, be present in sufficient quantity that, upon application of pressure, substantially every granule is in contact with a plurality of other granules, and preferably with three or more other granules. When the mixture is in condition for molding in accordance with the invention, and the outer surfaces of the polymer granules are softened to a tacky state, the points of contact between granules provide points of adhesion. Upon subsequent cooling of the article, the points of adhesion become strengthened to provide a strong bond. Thus, where the ratio of polymer particles to bioactive agent or other additive is sufficiently high, there exist sufficient points of contact to provide an article having good tensile strength.

It is important in the practice of the invention to avoid a molding temperature or pressure that is too high or too low. In the case of the former (i.e., excessive temperature and/or pressure), the article may become overly compacted, thereby causing the polymer to encase the bioactive agent resulting in an article which resembles a solid block and fails to prompt remodeling processes in an optimal manner. Where the temperature and/or pressure is too low, the resulting molded article may not have adequate tensile strength and, therefore, may have a tendency to crumble or break apart.

The polymer selected for use in accordance with the invention may be one of a wide variety of biocompatible polymers available commercially, as long as the polymer particles are suitable for molding under the conditions described herein. The physical properties of a given polymer are important to the determination of whether the polymer is suitable for use in a given implant material. With reference to the use of composites as spinal implants, it is desirable that the mechanical properties of an interbody implant device, such as, for example, an interbody fusion device, generally match those of the cancellous bone of the vertebrae in regard to proportional limit stress, compression at proportional limit, modulus of elasticity, failure stress and compression at failure. These structural features can be found in a wide variety of polymers known in the art that are also known to be biocompatible. As used herein, the term "biocompatible" refers to materials that, when implanted in a patient, do not induce undesirable long term effects. A preferred biocompatible material when introduced into a patient is not toxic or injurious to that patient, or does not cause immunological rejection.

Polymer particles suitable for use in accordance with the invention can be made from larger blocks of polymeric material via conventional milling processes. Following milling, the desired particle size range of the polymer may be recovered by sieving through, for example, U.S. Standard sieves. Particles in various size ranges, preferably less than 500 microns (e.g., size ranges of <45, 45-90, 90-125, 125-180, 180-250 microns) may be conveniently isolated or obtained and used in accordance with the invention. In one preferred embodiment, the particulate polymer has an average particle size of less than about 500 microns. In another embodiment, the polymer particles have an average particle size of less than about 400 microns. In selection of particle size range for use in accordance with the invention, it is sometimes desirable to combine two or more ranges, or to use a wide range of sizes, for instance all sizes less than 500 microns. Larger particles may be preferred in some applications of the invention because larger particles take longer to be eroded and will therefore extend the lifetime of the composite material in vivo should that be desired.

In certain preferred embodiments, the polymer used to form a composite according to the invention is a biodegradable polymer. As used herein, the terms "biodegradable," "bioerodable," "bioabsorbable" and "resorbable" are used interchangeably to refer to materials that degrade under physiological conditions to form a product that can be metabolized or excreted without damage to organs. Biodegradable materials may be hydrolytically degradable, may require cellular and/or enzymatic action to fully degrade, or both. Biodegradable materials also include materials that are broken down within cells. Degradation may occur by hydrolysis, enzymatic degradation, phagocytosis, or other methods.

When the invention is practices using a biodegradable polymer, once implanted the produced composites would initially have the strength and ductility comparable to the bone being treated, would retain these properties for a sufficient period of time for the bone to heal, and then would undergo benign and complete biodegradation, absorption, and/or excretion. In addition, in a preferred embodiment, the polymer is biodegradable at a rate consistent with regeneration or remodeling of the surrounding tissue. While it is not intended that the present invention be limited by any theory whereby it achieves its advantageous result, it is believed that implants formed of composite materials made from biodegradable polymers and including a bioactive agent that induces healing, advantageously provide good structural support while also promoting a mechanism of healing that includes remodeling of the bioactive agent and then transformation of the polymeric matrix.

As used herein, the term "remodeling" describes the process by which native bone, processed bone allograft, whole bone sections employed as grafts, other bony tissues and other bioactive agents are replaced with new cell-containing host bone tissue by the action of osteoclasts and osteoblasts.

Remodeling also describes the process by which non-bony native tissue and tissue grafts are removed and replaced with new, cell-containing tissue in vivo. As used herein, the term "transformation" describes the process by which a material is removed from an implant site and replaced by host tissue after implantation. Transformation may be accomplished by combination of processes, including but not limited to remodeling, degradation, resorption, and tissue growth and/or formation. Removal of the material may be cell-mediated or accomplished through chemical processes, such as dissolution and hydrolysis.

A variety of biodegradable polymer compositions can be selected for use in accordance with the present invention, provided that the selected polymer meets the requirements discussed herein. Exemplary biodegradable polymers include polylactides (also referred to as "poly(lactic acid)"), polycaprolactones (e.g., poly(F-caprolactone), polyglycolides (also referred to as "poly(glycolic acid)"), polyglyconate, poly-alpha-hydroxy ester acids, polyoxalates, and copolymers thereof, polyurethanes including glucose-based polyurethanes, polycarbonates, including trimethylene carbonate, polyiminocarbonates and tyrosine based polycarbonates, tyrosine based polyarylates and oxalate based polymers and copolymers, such as, for example, isomorphic ploy(hexamethylene co-trans-1,4-cyclohexane dimethylene oxalates). Examples of poly-alpha-hydroxy ester acids include polyhydroxyacetate, polyhydroxybutyrate, polyhydroxyvalerate, and copolymers thereof. Additional biodegradable polymers include poly(arylates), poly(anhydrides), poly ester amides, copoly(ether-ester), polyamide, polylactone, poly(hydroxy acids), polyesters, poly(ortho esters), poly(alkylene oxides), poly(propylene glycol-co fumaric acid), poly(propylene fumerates), polyamides, polyamino acids, polyacetals, poly (dioxanones), poly(vinyl pyrrolidone), biodegradable polycyanoacrylates, biodegradable poly(vinyl alcohols), polyphophazenes, polyphosphonates and polysaccharides, including chitosan. Co-polymers, mixtures, and adducts of any of these polymers may also be employed for use with the invention. Other examples of biodegradable polymers that are well known to those of ordinary skill in the art are described in Biomaterials Science—An Introduction to Materials in Medicine, edited by Ratner, B. D. et al., Academic Press, (1996).

Selection of a particular polymer is based primarily on the known properties of the polymer, such as, for example, the potentiality for cross-linking, polymer strength and moduli, rate of hydrolytic degradation and the like. One of ordinary skill in the art may take these and/or other properties into account in selecting a particular polymer for a particular application. Also pertinent to the selection of a particular polymer are the softening point of the polymer and/or the availability of a suitable binder for use therewith, as described herein. Thus, the selection of a particular polymer is within the skills of the ordinary skilled practitioner.

In a preferred embodiment, the polymer selected for use is a poly(L-lactide-co-D,L-lactide) (also referred to herein as "PLA"). One particularly preferred PLA polymer for use in the device of the invention is Resomer™ LR 708 (commercially available from Boehringer-Ingelheim), which has a weight average molecular weight of 800 kg/mol to 1200 kg/mol as measured by gel permeation chromatography (GPC).

In another preferred embodiment, the polymer selected for use is a lactide-glycolide copolymer of any ratio (e.g., 85:15, 40:60, 30:70, 25:75, or 20:80) (also referred to herein as "poly(lactide-co-glycolide)" or "PLGA"). The ratios provided in the preceding sentence refer to the mole ratio of lactide to glycolide in the polymer. The PLGA polymer selected for use in accordance with the invention can have a lactide to glycolide ratio in the range of 0:100% to 100:0%, inclusive, i.e., the PLGA polymer can consist of 100% L- or D,L-lactide (PLA), 100% glycolide (PGA), or any combination of lactide and glycolide residues. One particularly preferred PLGA polymer for use in the device of the invention is poly(d,1-lactide-co-glycolide)-85:15 (Boehringer-Ingelheim). A commercial name of this polymer is Resomerm RG 858, which has a weight average molecular weight of 232,000 as measured by gel permeation chromatography (GPC).

It has been reported that the process by which alpha polyesters such as PLA, PGA, and PLGA biodegrade is primarily by non-specific hydrolytic scission of the ester bonds in vivo to form organic acids (lactic acid and glycolic acid) which accumulate in the region surrounding the implant. These acids are metabolized and eventually excreted as carbon dioxide and water or enter the citric acid cycle. The L-lactic acid that is generated when PLA or PLGA degrades is believed to become incorporated into the tricarboxylic acid cycle and is excreted from the lungs as carbon dioxide and water. Glycolic acid, produced both by random hydrolytic scission and by enzymatically mediated hydrolysis, may be excreted in the urine and also can enter the TCA cycle and eventually be oxidized to carbon dioxide and water.

Persons skilled in the art will also appreciate that polymers selected for use in inventive methods may be manipulated to adjust their degradation rates. The degradation rates of polymers are well characterized in the literature (see Handbook of Biodegradable Polymers, Domb, et al., eds., Harwood Academic Publishers, 1997, the entire contents of which are incorporated herein by reference). In addition, increasing the cross-link density of a polymer tends to decrease its degradation rate. The cross-link density of a polymer may be manipulated during polymerization by adding a cross-linking agent or promoter. After polymerization, cross-linking may be increased by exposure to UV light or other radiation. Co-monomers or mixtures of polymers, for example, lactide and glycolide polymers, may be employed to manipulate both degradation rate and mechanical properties.

In addition to the biodegradable polymers discussed above, non-biodegradable polymers may also be employed for use in some embodiments of the invention. Exemplary non-biodegradable, yet biocompatible polymers include polystyrene, polyesters, polyureas, poly(vinyl alcohol), polyamides, poly (tetrafluoroethylene), and expanded polytetrafluroethylene (ePTFE), poly(ethylene vinyl acetate), polypropylene, polyacrylate, non-biodegradable polycyanoacrylates, non-biodegradable polyurethanes, mixtures and copolymers of poly (ethyl methacrylate) with tetrahydroftirftiryl methacrylate, polymethacrylate, poly(methyl methacrylate), polyethylene, including ultra high molecular weight polyethylene (UHMWPE), polypyrrole, polyanilines, polythiophene, poly(ethylene oxide), poly(ethylene oxide co-butylene terephthalate), poly ether-ether ketones (PEEK), and polyetherketoneketones (PEKK).

A wide variety of bioactive materials can be selected for use in accordance with the present invention. As used herein, the term "bioactive agent" is used to refer to a compound or entity that alters, inhibits, activates, or otherwise affects biological or chemical events. For example, bioactive agents may include, but are not limited to osteogenic, osteoinductive, and osteoconductive agents, anti-AIDS substances, anti-cancer substances, antibiotics, immunosuppressants (e.g., cyclosporine), anti-viral agents, enzyme inhibitors, neurotoxins, opioids, hypnotics, anti-histamines, lubricants, tranquilizers, anti-convulsants, muscle relaxants and anti-Parkinson agents, anti-spasmodics and muscle contractants including channel blockers, miotics and anti-cholinergics, anti-glaucoma compounds, anti-parasite, anti-protozoal, and/or anti-fungal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, targeting agents, neurotransmitters, proteins, cell response modifiers, and vaccines. In a certain preferred embodiments, the bioactive agent is a drug.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals," Edited by Susan Budavari et al., CRC Press, 1996, the United States Pharmacopeia-25/National Formular-20, published by the United States Pharmcopeial Convention, Inc., Rockville Md., 2001, and the "Pharmazeutische Wirkstoffe," edited by Von Keemann et al., Stuttgart/New York, 1987, all of which are incorporated herein by reference. Drugs for human use and drugs for veterinary use listed by the FDA in the Code of Federal Regulations, all of which is incorporated herein by reference, are also considered acceptable candidates for use in accordance with the present invention.

In certain preferred embodiments, the bioactive agent is a biomolecule or comprises a biomolecule. The term "biomolecule," as used herein, refers to a class of molecules (e.g., proteins, amino acids, peptides, polynucleotides, nucleotides, carbohydrates, sugars, lipids, nucleoproteins, glycoproteins, lipoproteins, steroids, lipids, etc.) that are commonly found in cells and tissues, whether the molecules themselves are naturally-occurring or artificially created (e.g., by synthetic or recombinant methods). For example, biomolecules include, but are not limited to, enzymes, receptors, glycosaminoglycans, neurotransmitters, hormones, cytokines, cell response modifiers such as growth factors and chemotactic factors, antibodies, vaccines, haptens, toxins, interferons, ribozymes, anti-sense agents, plasmids, DNA, and RNA. Exemplary growth factors include but are not limited to bone morphogenic proteins (BMP's) and their active subunits. In some embodiments, the biomolecule is a growth factor, cytokine, extracellular matrix molecule or a fragment or derivative thereof, for example, a cell attachment sequence such as RGD. Bioactive agents selected for use in accordance with the invention include synthetic bioactive agents and bioactive agents that are isolated or derived from natural sources. Examples of preferred bioactive agents include bone, bone morphogenic protein and growth factors including for example transforming growth factor-β.

In one preferred embodiment, the bioactive material is a particulate material having an average particle size of less than about 80 microns. One preferred bioactive agent comprises bone particles milled from whole bone or bone sections. As used herein, the term "bone" is intended to refer to bone recovered from any source including animal and human, for example, human bone recovered for the production of allografts, and animal bone recovered for the production of xenografts, such allografts and xenografts suitable for implantation into a human. Such bone includes: any bone or portion thereof, including cut pieces of bone, including cortical and/or cancellous bone, for example, recovered from a human including a living human or a cadaver, or animal, and processed for implantation into a living patient. Such bones include for example: the humorous, hemi-pelvi, tibia, fibula, radius, ulna, rib, vertebrae, mandibular, femur, and ilia, and any cut portion thereof Such bone may be demineralized or not demineralized. The bone can be demineralized or non-demineralized in alternate embodiments. Reduction of the antigenicity of allogeneic and xenogeneic tissue can be achieved by treating the tissues with various chemical agents, e.g., extraction agents such as monoglycerides, diglycerides, triglycerides, dimethyl formamide, etc., as described, e.g., in U.S. Pat. No. 5,507,810, the contents of which are incorporated by reference herein.

The bioactive agent can comprise either intact extracellular matrix or its components, alone or in combination, or modified or synthetic versions thereof. Exemplary extracellular matrix components include but are not limited to collagen, laminin, elastin, proteoglycans, reticulin, fibronectin, vitronectin, glycosaminoglycans, and other basement membrane components. Various types of collagen (e.g., collagen Type I, collagen Type II, collagen Type IV) are suitable for use with the invention. Collagens may be used in fiber, gel, or other forms. Sources for extracellular matrix components include, but are not limited to, skin, tendon, intestine and dura mater obtained from animals, transgenic animals and humans. Extracellular matrix components are also commercially available.

To make a composite material in accordance with the invention, the particulate polymer and the bioactive agent are first thoroughly mixed. The polymer and the bioactive agent may be combined using standard composite processing techniques. For example, the materials can be mixed in a rotational mixer. The mixture of polymer particles and bioactive material to be molded preferably has a polymer-to-bioactive ratio of from about 1:2 to about 9:1 by weight (i.e., the polymer comprises from about 33% to about 90% of the combined polymer and bioactive material components, by weight). More preferably, the ratio is from about 1:1 to about 9:1 by weight (i.e., about 50% to about 90% polymer, by weight).

In one preferred aspect of the invention, prior to molding of the mixture, the polymeric material is treated with a binder that is effective to promote polymer particle adhesion, and thereby improve the mechanical properties of the molded composite. The use of a binder as described herein can also have the advantageous result of enabling the use of modified processing parameters. In a preferred embodiment, the binder is a liquid binder that is present in an amount effective to contact at least a majority of the polymer particles in the mixture after thorough mixing. In one preferred embodiment, the binder is a solvent in which the polymer that is selected for use in the composite is soluble. After a small amount of solvent is added to the mixture, the surfaces of the polymer particles are expected to form a thin layer of solvent/polymer solution. While it is not intended that the invention be limited by any theory whereby it achieves its advantageous result, it is believed that the polymer chains can entangle with each other more easily in solution than in solid form, and the layer of solvent/polymer solution at the surfaces of the polymer particles is therefore expected to promote the adherence of particles to one another when molded under pressure.

A person of ordinary skill in the art will recognize that the selection of a suitable solvent will depend upon the identification of the polymer that is used to form a given composite, as well as compatibility with the bioactive agent and any other materials that are present in the mixture to be molded. In one embodiment, a preferred solvent for use in accordance with the invention is a solvent that has a boiling point slightly lower than the molding temperature. When the boiling point of the solvent is slightly lower than the molding temperature, the solvent may be vaporized during the molding process, which will promote solvent removal from the polymer. As one excellent example, in an embodiment in which particulate polylactide polymer is used to form the porous plastic matrix in accordance with the invention, a suitable solvent is tetrahydrofuran (THF). Other exemplary solvents that can be used in connection with polymers contemplated by the invention include halogenated carbons, ketones, aldehydes, alcohols, esters, ethers, hydrocarbons, DMSO and DMAC.

In another embodiment, the binder that is mixed with the particulate polymer and bioactive material comprises a solvent/polymer solution. It is believed that a solution of polymer in a solvent will operate similarly to a solvent alone by providing a thin layer of dissolved polymer on the surfaces of the polymer particles, which is expected to promote the adherence of particles when molded under pressure. In a preferred embodiment, the polymer dissolved in the solvent is of the same compositional nature as the particulate polymer in the mixture. The invention also contemplates, however, that diverse polymers can be used to advantage in other embodiments.

After the starting materials are thoroughly mixed, the composite material is made by subjecting the mixture to a predetermined pressure at a predetermined temperature for a predetermined period of time to achieve molding. The pressure is applied, for example, in a pressurized mold under such circumstances that the structure of at least a portion of the polymer particles are partially dissolved, softened or melted. Under the pressure, the dissolved, softened or melted surfaces of particles or corresponding structures are coalesced together and when the mold is cooled, a strong composite structure is obtained. By a careful control of the heating conditions it is possible to process composite samples where the dissolved, softened or melted surface regions of the particles are very thin and, therefore, the high strength of the structure can be accomplished without applying extremely high temperatures, thereby leading to materials with high tensile, shear, bending and impact strength values, while also retaining the bioactive function provided by the bioactive agent.

In one embodiment, the particulate polymer, bioactive material and binder mixture is formed into a composite material by injection molding. Alternatively or in addition, the mixture can be combined and pressed in a Carver press or other compression molding device. Exemplary pressures include pressures ranging from about 1000 PSI to about 40,000 PSI. In a preferred embodiment, the pressure is from about 10,000 PSI to about 30,000 PSI. The particular pressure to be used will depend on the materials being pressed.

In addition to the application of pressure, in some embodiments heat is applied to bring the mixture to a temperature at least as high has the softening temperature or glass transition temperature of the polymer (i.e., a temperature suitable to soften the amorphous portion of the polymer) but not to a temperature at which the crystalline structure melts (i.e., the melting temperature), or a temperature at which an adverse effect upon the functionality of the bioactive agent would occur. Preferably, the temperature is chosen from a range between the softening point and the melting point of the polymer. Indeed, some suitable polymers whose softening points are sufficiently low (i.e., within a range of about 70° C. to about 100° C.) can be advantageously molded to form good composite materials without adding a binder due to the softening of the surfaces of polymer particles at such a relatively low temperature.

In some embodiments, the molding temperature is from about 70° C. to about 80° C. One skilled in the art will recognize that higher temperatures may be needed, and that the processing temperature may be optimized to allow the polymer to be processed as long as the temperature is not raised to a point that results in damage to other components of the composite. A person of ordinary skill in the art will understand that the inclusion of a binder in the mixture can modify the softening temperature. In embodiments in which a binder is present, it is understood that the softening point at the surface of a polymer, as modified by the binder, might be lower than the natural softening point of the polymer in the absence of the binder. In other words, temperatures below the natural softening point of the polymer may be suitable molding temperatures in embodiments in which the binder is effective to soften the surface of the polymer at a temperature below its natural softening temperature.

Thus, the invention provides in one aspect a method for making a biomaterial composite that is bioactive and is suitable for use as a medical implant that includes (1) providing a bioactive material that is stable up to a first temperature; (2) providing a particulate biocompatible polymer; (3) mixing the particulate polymer and the particulate bioactive material together with a binder to form a mixture, wherein the binder is effective to soften the particulate polymer at a second temperature less than the first temperature; and (4) compressing the mixture at a third temperature less than the first temperature and greater than the second temperature for a period of time sufficient to allow at least a majority of the polymer particles to adhere to one another. In one preferred manner of practicing the invention, at the end of the period of time during which the compression is applied, the mold is cooled to room temperature or lower under the compressive force. In one particularly preferred embodiment, the polymer is a polylactide polymer. The ratio of polymer to bioactive material in the mixture by weight is preferably from about 1:2 (by weight) to about 9:1 (by weight). The binder preferably comprises tetrahydrofuran.

In addition to the polymer, the bioactive agent and the binder, other ingredients can optionally be included in the mixture used to make a composite material in accordance with the invention. For example, some ingredients can be included to increase the stability or shelf life of the bioactive agent included in the composite. Other ingredients can be selected to provide an advantageous effect after the composite material is implanted. An example of the latter is a buffer, which finds advantageous use in connection with certain biodegradable polymers. As certain biodegradable polymers undergo hydrolysis in the body, acidic degradation products formed may be implicated in irritation, inflammation, and swelling (sterile abscess formation) in the treated area. To counteract this effect, a neutralization compound, or buffer, can be included in the biodegradable material to neutralize the acidic degradation products and thereby reduce the sterile abscess reaction.

The buffering compound included in the biodegradable material of the invention may be any base, base-containing or base-generating material that is capable of reacting with the acidic products generated upon hydrolysis of the biodegradable polymer. Exemplary buffering materials include salts of inorganic or organic acids, salts of polymeric organic acids or polymeric bases such as polyamines. Preferably calcium salts of weak acids such as, e.g., tribasic calcium phosphate, dibasic calcium phosphate, or calcium carbonate are use. To be useful, the conjugate acids from which the buffering materials are derived must have a pKa greater than those of L-lactic acid (pKa=3.79), D,L-lactic acid (pKa=3.86), or glycolic acid (pKa=3.83), if a PLGA is the polymer which is undergoing hydrolysis. Thus, for example, salts of acetic acid (pKa=4.74), or succinic acid ($pK_1$=4.19, $pK_2$=5.64) may also be used.

Buffer compositions of lower solubility are preferred because buffer loss from the polymer by diffusion will be slower. Preferably, the buffering compound has an acid dissociation constant that is smaller than the acid dissociation constant of the acidic products generated upon hydrolysis of the biodegradable polymer. Ionic buffers will, in general, be the salts of weak acids. The acid, of which the buffer is a salt, should have an ionization constant (acid dissociation constant, $K_a$) which is less than the $K_a$ for the acid products of polymer hydrolysis. Alternatively, the buffering compound has a hydrolysis constant that is greater than the hydrolysis constant of the acidic products. Hydroxyapatite (HA) and calcium carbonate (CC) can be included in a composite made in accordance with the invention using, e.g., PLGA, as a buffering agent to moderate the rate of pH decline as the composite material degrades in vivo.

In addition to ameliorating the rate of decline in pH in the region of polymer hydrolysis, the use of hydroxyapatite also supports osteoconductivity. Thus, HA not only promotes bony ingrowth and obviates loosening of the implant, but also acts as a buffer thereby preventing the formation of sterile abscesses that have been attributed to the acidic degradative products of PLGA implants. The resulting resorbable implant should be capable of a buffered hydrolytic degradation and induction of bony ingrowth as resorption of the implant progresses. A resorbable buffered bone implant with such properties could provide structural support to stabilize and support a spinal repair over the period of time required for natural healing to occur.

Buffers included in the polymer in solid form preferably have a relatively small particle size, for example, between less than 1.0 and 250 microns. Particle size reduction can be accomplished by any standard means known in the art, such as ball milling, hammer milling, air milling, or the like. If buffer and polymer are to be blended using a dry mixing method, the polymer particle size must also be considered. Furthermore, since polymers such as the PLGAs have relatively low glass transition temperatures and melting temperatures, polymer particle size reduction must be accompanied by cooling, for example using a Tekmar A-10 mill with a cryogenic attachment.

The final performance of a composite material made in accordance with the invention is influenced, for example, by its degradation rate and mechanism, component porosity, activity of bioactive agent and component mechanical properties including strength, fracture toughness, and modulus. While many polymers degrade from the surface in, penetration of cells into the interior of the composite can increase the overall degradation rate and cause more uniform degradation across a cross-section of the composite material. Both the inherent porosity of the composite and induced pathways influence the overall composite degradation rate by facilitating the infiltration of cells into the composite.

One advantage of composites made in accordance with the invention is that, following implantation into a living host, they either completely or partially transform into host tissue. As long as the pores and internal passages are made to have sufficient dimensions, host cells are able to penetrate and stabilize the composite with host tissue prior to substantial resorption or degradation of the overall construct or its components. Transformation may occur through the active replacement of all or portions of the composite construct by penetrating cells, or by cellular penetration into the construct with subsequent replacement or degradation of the composite or one or more of its components. As will be readily recognized, the thickness of the composite material made in accordance with the invention will also have an impact upon the rate at which it degrades and total degradation time.

Dimensions of the internal passages and pores of an inventive composite material can be varied, for example, by selecting polymer granules having larger or smaller sizes, by adjusting the process temperature or process pressure at which inventive articles are molded, and/or by varying the ratio of polymer granules to bioactive material and other ingredients in a mixture to be molded. In one preferred aspect of the invention, the pores have an average size of from about 1 to about 1000 microns. More preferably, the pores have an average size of from about 100 microns to about 800 microns.

Molding processes described herein can advantageously be used to make composite materials having a wide variety of shapes and sizes for various different uses. In one preferred embodiment, an implant device is made by molding the composite material into a desired shape using a mold having the specific desires shape. Alternatively, or in addition, the composite can be machined after molding using cutting tools known in the art to provide porous plastic composite articles having any desired shape and size. Exemplary shapes include sheet, plate, sphere, hemisphere strand, coiled strand, disk, cone, portion of a cone, pin, screw, tube, bone, portion of bone, strut, wedge, portion of wedge, cylinder, threaded cylinder, rod, hinge, rivet, anchor, spheroid, ellipsoid, oblate spheroid, prolate ellipsoid, hyperbolic paraboloid. Exemplary bones whose shape the composite may match in whole or in part (and which may be repaired or replaced using the techniques of the invention) include ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, incus, malleus, stapes, ilium, ischium, pubis, femur, tibia, fibula, patella, calcaneus, tarsal and metatarsal bones. Composites can be molded into any of these shapes as well, obviating a machining step or reducing the amount of machining needed.

In an alternative embodiment, bores or holes may be introduced into the composite. Such holes may be drilled after the composite is formed. Alternatively or in addition, the mold may be formed with pegs to introduce holes into the composite. Such holes may be used to provide an anchor for sutures, screws, or other fasteners. Of course, cells will also migrate into the hoe after implantation.

Whether or not the composite is expected to be completely infiltrated within a predetermined period of time, it desirably has sufficient mechanical strength to withstand physiological loads until it is fully transformed. In one embodiment, the composite has a yield strength in aqueous environments of about 20 MPa or greater, more preferably about 30 MPa or greater, and still more preferably about 40 MPa or greater, and an initial wet stiffness of 1 GPa or greater. Fatigue life may be greater than 1.25 million cycles or, for example, at least 3 million cycles, at 25 MPa. As the material degrades, it may retain some mechanical strength, for example, having at least 25 MPa residual strength after 6 months in vivo. Alternatively, it may maintain at least 70% of their original strength after 24 weeks. The degradation rate of the polymeric matrix may be matched to the rate at which surrounding tissue can interpenetrate the implant or remodel injured tissue surrounding the implant. Of course, the desired mechanical properties depend on the specific implant application. For example, a bone void filler can transform quickly and need not have high mechanical strength, while a lumbar interbody implant may need to exhibit substantially higher compressive and fatigue strength as it is transformed.

The invention will be further described with reference to the following specific Examples. It will be understood that these Examples are intended to be illustrative and not restrictive in nature.

EXAMPLES

The polymer tested in the following Examples was the bioabsorbable polymer poly (L co D,L-lactide) (hereafter "PLA") marketed under the name Resomer® LR708 by Boehringer Ingelheim (Germany). The bioactive material used in the Examples was bovine bone.

Both the bone and the PLA were ground into powder form. The particle size of the PLA powder was less than 500 µm and the bone powder was less than 80 µm. All of the powder was stored within a dessicator until used in order to minimize moisture damage.

Example One

Binder-Aided Powder Molding Using a Solvent

The polymer and bone powder were weighed out according to the weight percent desired in the final product. To the polymer and bone powder was added tetrahydrofuran (THF) as a binder in an amount of from about 3 to about 5 weight percent based on total powder. The mixture of the PLA powder, bone powder and binder were mixed with a rotational mixer (Speed Mixer™ DAC 150FV by FlackTech Inc., South Carolina) at 3000 rpm for 30 seconds. The resulting mixture was then briefly stirred by hand using a spatula for a few seconds and immediately placed into a compression mold that had already been heated to 75-78° C. The mold was closed and a compression stress of 10,000 to 25,000 PSI was applied for 30 minutes. After this, the mold was turned over and pressed again at the same temperature and pressure for 30 more minutes. After this processing, the mold was cooled to room temperature with the same pressure held. The composite was immediately pressed out of the mold. Great care was made to ensure that the minimum force was used when removing a composition from the mold since too much pressure could crack the composite. Then the molded composite part was placed into a sealed plastic bag and stored in a desiccator until future use.

Example Two

Binder-Aided Powder Molding Using a Solvent/PLA Solution

The process in accordance with Example 1 was followed with the exception that the binder used was a solution of PLA in THF at a concentration of 3 or 5 weight percent.

Example Three

Dry Powder Molding

The process in accordance with Example 1 was followed with the exception that the binder was omitted. The mixture placed in the mixer was a "dry" powder mixture.

Example Four

Strength Testing of Molded Articles

All samples produced in accordance with Examples 1-3 were soaked in water at room temperature for two weeks. Compression tests were conducted with an MTS testing system. The results, which are provided in Tables I and II below, demonstrate that good mechanical properties can be achieved using low-temperature powder molding processing in accordance with the present invention. However, when the bone content was high (i.e., about 50 weight percent), the parts molded from the dry powder mixtures broke automatically after being soaked in water for a few hours. The mechanical strength was zero (Table II). This suggested that the binders had the effect to promote the mechanical integrity of the molded composite parts.

TABLE I

Testing of Articles Made using a PLA and Bone Powder Mixture Comprising 85% PLA by Weight and 15% Bone by Weight

| Molding Method Compression of: | Compression Strength (MPa) |
|---|---|
| powder with solvent (Example 1) | 15 |
| powder with solution (Example 2) | 20 |
| dry powder (Example 3) | 30 |

TABLE II

Testing of Articles Made using a PLA and Bone Powder Mixture Comprising 50% PLA by Weight and 50% Bone by Weight

| Molding Method Compression of: | Compression Strength (MPa) |
|---|---|
| powder with solvent (Example 1) | 35 |
| powder with solution (Example 2) | 47 |
| dry powder | 0 |

As seen in the above tables, the compression strength was about 10 to 40 MPa for the two compositions tested in which binders were used during the molding process. These compression strength values are comparable to compression strengths of components made using protocols in which the polymer is dissolved in solvents; however, the powder molding procedure of the invention is much faster than procedures that require dissolution of the polymer.

The results set forth above indicate that high strength porous plastic articles can be achieved using inventive powder molding processes. In addition to those results set forth above, a cylinder molded with the above procedure from pure PLA powder with particle size less than 500 µm was tested, and shown to have a compression strength of about 90 MPa, which is similar to that of PEEK, which exhibited a compression strength of about 120 MPa in similar testing. The tensile strength reported in the literature for melt processed PLA is about 30 to 50 MPa. Thus, lower-temperature powder molding in accordance with the invention can provide similar high strength articles as the melt processing method.

While the invention has been described in detail in the foregoing description, the same is to be considered illustrative and not restrictive in character, it being understood that only selected embodiments have been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a," "an," "at least one" and "at least a portion" are not intended to limit the claims to only one item unless specifically stated to the contrary. Further, when the language "at least a portion" and/or "a portion" is used, the claims may include a portion and/or the entire item unless specifically stated to the contrary. The following definitions and meanings are also considered pertinent in reading the descriptions in the present specification. "Polynucleotide," "nucleic acid" or "oligonucleotide": The terms "polynucleotide," "nucleic acid" or "oligonucleotide" refer to a polymer of nucleotides. The terms "polynucleotide," "nucleic acid" and "oligonucleotide" may be used interchangeably. Typically, a polynucleotide comprises at least two nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thihymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyriboses, arabinose, and hexose), or modified phosphate groups (e.g., phosphorothioates and 5'-N-phosphoramidite linkages). The polymer may also be a short strand of nucleic acids such as siRNA.

"Polypeptide," "peptide" or "protein": As used herein, a "polypeptide," "peptide" or "protein" includes a string of at least two amino acids linked together by peptide bonds. The terms "polypeptide," "peptide" and "protein" may be used interchangeably. Peptide may refer to an individual peptide or a collection of peptides. In some embodiments, peptides may contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

The terms "polysaccharide" or "oligosaccharide," as used herein, refer to any polymer or oligomer of carbohydrate residues. The polymer or oligomer may consist of anywhere from two to hundreds to thousands of sugar units or more. "Oligosaccharide" generally refers to a relatively low molecular weight polymer, while "starch" typically refers to a higher molecular weight polymer. Polysaccharides may be purified from natural sources such as plants or may be synthesized de novo in the laboratory. Polysaccharides isolated from natural sources may be modified chemically to change their chemical or physical properties (e.g., phosphorylated, cross-linked). Carbohydrate polymers or oligomers may include natural sugars (e.g., glucose, fructose, galactose, mannose, arabinose, ribose, and xylose) and/or modified sugars (e.g., 2'-fluororibose, 2'-deoxyribose, and hexose). Polysaccharides may also be either straight or branch-chained. They may contain both natural and/or unnatural carbohydrate residues. The linkage between the residues may be the typical ether linkage found in nature or may be a linkage only available to synthetic chemists. Examples of polysaccharides include cellulose, maltin, maltose, starch, modified starch, dextran, and fructose. Glycosaminoglycans are also considered polysaccharides. Sugar alcohol, as used herein, refers to any polyol such as sorbitol, mannitol, xylitol, galactitol, erytthritol, inositol, ribitol, dulcitol, adonitol, arabitol, dithioerythritol, dithiothreitol, glycerol, isomalt, and hydrogenated starch hydrolysates.

What is claimed is:

1. A method for making a biomaterial composite that is bioactive and is suitable for use as a medical implant, comprising:
    providing a bioactive material that is comprised of a biomolecule that is stable up to a first temperature;
    milling a block of polymeric material to form a particulate biocompatible polymer, the particulate biocompatible polymer comprising PLGA;
    mixing the particulate biocompatible polymer and the bioactive material together with a binder at a second temperature to form a mixture, wherein the binder comprises a solvent/polymer solution comprising dimethylacetamide (DMAC) and the binder is effective to soften surfaces of the particulate biocompatible polymer at the second temperature, the second temperature being less than the first temperature;
    adding a buffer comprising a calcium salt comprising calcium phosphate to the mixture, the buffer having a particle size of between less than 1.0 and 250 micrometers and a pKa greater than 3.79; and
    compressing the mixture at a third temperature less than the first temperature and greater than the second temperature for a period of time sufficient to allow at least a majority of the polymer particles to adhere to one another, and, at the end of the period of time, cooling the mixture to room temperature under a compressive force to form the biomaterial composite and pores in the biomaterial composite that have an average size range of from about 100 to about 800 microns, wherein the biomaterial composite has a compression strength of about 10 MPa to about 40 MPa, wherein the third temperature is a glass transition temperature of the PLGA.

2. The method in accordance with claim 1 wherein the ratio of polymer to bioactive material in the mixture by weight is from about 1:2 to about 9:1.

3. The method in accordance with claim 1 wherein the bioactive material is particulate bone.

4. The method in accordance with claim 1 wherein the bioactive material is a particulate material having an average particle size of less than about 80 microns.

5. The method in accordance with claim 1 wherein the particulate biocompatible polymer has an average particle size of less than about 500 microns.

6. The method in accordance with claim 1 wherein said compressing comprises compressing under a compressive stress of from about 10,000 PSI to about 25,000 PSI.

7. The method in accordance with claim 1 wherein the binder is present in an amount effective to contact at least a majority of the polymer particles.

8. The method in accordance with claim 1 wherein said compressing is accomplished in an injection mold.

9. The method in accordance with claim 1, wherein the biomolecule comprises at least one of a protein, an amino acid, a peptide, a polynucleotide, a glycoprotein, a lipoprotein, a steroid or lipid.

10. The method according to claim 1, wherein the calcium phosphate is tribasic calcium phosphate.

11. The method according to claim 1 wherein the PLGA is poly(d,l-lactide-co-glycolide) having a mole ratio between lactide and glycolide of 85:15.

12. The method according to claim 1 wherein the PLGA has a mole ratio between lactide and glycolide of 20:80.

13. The method according to claim 1 wherein the biomaterial composite comprises a network of internal passages in fluid communication with an environment of the biomaterial composite through the pores.

14. The method according to claim 13 wherein the internal passages are interconnected.

15. The method according to claim 1 wherein a weight of the biocompatible polymer comprises from about 33% to about 90% of a combined weight of the biocompatible polymer and the bioactive material.

16. The method according to claim 3 wherein the bone is demineralized and has an average particle size of less than about 80 microns.

* * * * *